United States Patent
Allegretti et al.

(10) Patent No.: US 7,026,510 B2
(45) Date of Patent: Apr. 11, 2006

(54) QUATERNARY AMMONIUM SALTS OF OMEGA-AMINOALKYLAMIDES OF R-2-ARYL-PROPIONIC ACIDS AND PHARMACEUTICAL COMPOSITIONS CONTAINING THEM

(75) Inventors: Marcello Allegretti, L'Aquila (IT); Riccardo Bertini, L'Aquila (IT); Cinzia Bizzarri, L'Aquila (IT); Maria Candida Cesta, L'Aquila (IT)

(73) Assignee: Dompé S.p.A., L'Aquila (IT)

( * ) Notice: Subject to any disclaimer, the term of this patent is extended or adjusted under 35 U.S.C. 154(b) by 98 days.

(21) Appl. No.: 10/487,679

(22) PCT Filed: Sep. 25, 2002

(86) PCT No.: PCT/EP02/10746
§ 371 (c)(1),
(2), (4) Date: Apr. 8, 2004

(87) PCT Pub. No.: WO03/029187
PCT Pub. Date: Apr. 10, 2003

(65) Prior Publication Data
US 2004/0266870 A1    Dec. 30, 2004

(30) Foreign Application Priority Data
Sep. 28, 2001   (IT) .......................... MI2001A2025

(51) Int. Cl.
C07C 233/05    (2006.01)
A61K 31/165    (2006.01)

(52) U.S. Cl. ................ 564/182; 564/181; 562/455; 544/59; 544/168; 546/216; 546/224; 546/225; 514/227.5; 514/237.8; 514/327; 514/329; 514/330; 514/538; 514/617; 514/619

(58) Field of Classification Search ................ 564/163, 564/182; 562/455; 546/216, 224, 225; 544/59, 544/168; 514/617, 619, 327, 329, 330, 538, 514/227.5, 237.8
See application file for complete search history.

(56) References Cited

U.S. PATENT DOCUMENTS

2002/0160988 A1* 10/2002 Amitai et al. ................ 514/159

FOREIGN PATENT DOCUMENTS

| FR | 1 593 024 A | 5/1970 |
| FR | 2 410 641 A | 6/1979 |
| WO | WO 01 58852 A | 8/2001 |
| WO | WO 02 068377 A | 9/2002 |

* cited by examiner

Primary Examiner—Shailendra Kumar
(74) Attorney, Agent, or Firm—Birch, Stewart, Kolasch & Birch, LLP

(57) ABSTRACT

(R)-Enantiomers of quaternary ammonium salts of general formula (I) are described:

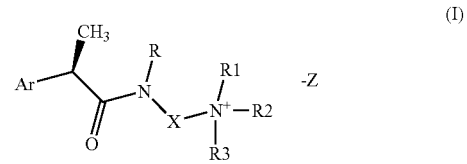

where R, $R_1$, $R_2$, $R_3$, X and Z are as defined in the description.

The process for their preparation and pharmaceutical preparations thereof are also described.

The quaternary salts of the invention are useful in the inhibition of chemotaxis of neutrophils and monocytes induced by the fraction C5a of the complement and are used in the treatment of psoriasis, pemphigus and pemphigoid, rheumatoid arthritis, intestinal chronic inflammatory pathologies including ulcerative colitis, acute respiratory distress syndrome, idiopathic fibrosis, cystic fibrosis, chronic obstructive pulmonary disease and glomerulonephritis.

The compounds of the invention are advantageously used in the prevention and the treatment of injury caused by ischemia and reperfusion.

17 Claims, No Drawings

QUATERNARY AMMONIUM SALTS OF OMEGA-AMINOALKYLAMIDES OF R-2-ARYL-PROPIONIC ACIDS AND PHARMACEUTICAL COMPOSITIONS CONTAINING THEM

This application is a 371 of PCT/EP02/10746, filed Sep. 25, 2002.

INTRODUCTION AND BACKGROUND OF THE INVENTION

The present invention relates to compounds useful in the inhibition of the chemotactic activation induced by the fraction C5a of complement and from other chemotactic proteins (chemokines) that exert their action by activating a 7-transmembrane-domain (7-TM) receptor. Said compounds are quaternary ammonium salts of R-2-arylpropionamides useful in the treatment of pathologies depending on the chemotactic activation of neutrophils and monocytes induced by the fraction C5a of the complement. In particular, the compounds of the invention are useful in the treatment of psoriasis, rheumatoid arthritis, ulcerative colitis, acute respiratory distress syndrome, idiopathic fibrosis, glomerulonephritis and in the prevention of injury caused by ischemia and reperfusion.

DETAILED DESCRIPTION OF THE INVENTION

The present invention relates to (R)-2-aryl-propionamides of formula (I):

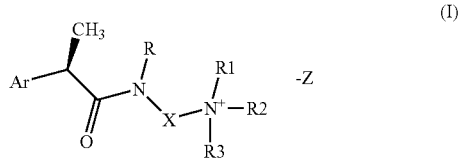

wherein

Ar represents a substituted or non-substituted aryl group;

R represents hydrogen, $C_1$–$C_4$ alkyl, $C_2$–$C_4$ alkenyl, $C_2$–$C_4$ alkynyl, optionally substituted by a $CO_2R_4$ group, wherein $R_4$ represents hydrogen or a linear or branched $C_1$–$C_6$ alkyl group or a linear or branched $C_2$–$C_6$ alkenyl group;

X represents:

linear or branched $C_1$–$C_6$ alkylene, $C_4$–$C_6$ alkenylene, $C_4$–$C_6$ alkynylene, optionally substituted by a $CO_2R_4$ group or by a $CONHR_5$ group wherein $R_5$ represents hydrogen, linear or branched $C_2$–$C_6$ alkyl or an $OR_4$ group, $R_4$ being defined as above;

phenyl or a phenylmethylene group of formula:

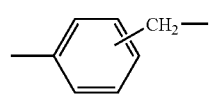

a $(CH_2)_m$—B—$(CH_2)_n$ group, optionally substituted by a $CO_2R_4$ or $CONHR_5$ group, as defined above, wherein B is an oxygen or sulfur atom, m is zero or an integer from 2 to 3 and n is an integer from 2 to 3; or B is a CO, SO or CONH group, m is an integer from 1 to 3 and n is an integer from 2 to 3;

or X together with the nitrogen atom to which it is bound and with the $R_1$ group forms a nitrogen containing 3–7 membered heterocyclic monocyclic or polycyclic ring;

$R_1$, $R_2$ and $R_3$ are independently linear or branched $C_1$–$C_6$ alkyl, optionally substituted by an oxygen or sulfur atom, a $C_3$–$C_7$ cycloalkyl, $C_3$–$C_6$ alkenyl, $C_3$–$C_6$-alkynyl, aryl, aryl-$C_1$–$C_3$-alkyl, hydroxy-$C_2$–$C_3$-alkyl group;

or $R_1$ and $R_2$ together with the N atom to which they are bound, form a nitrogen containing –3–7 membered heterocyclic ring of formula (II) and R3 independently has the meanings as defined above.

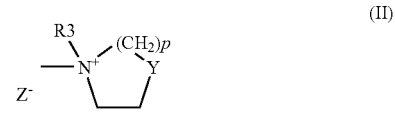

In the general formula (II)

Y represents a single bond, a methylene group, an oxygen atom, a nitrogen atom or a sulfur atom p represents an integer from 0 to 3;

Z represents conventional anions used as counter-ions of quaternary ammonium salts which are pharmaceutically acceptable, such as, for example, halide ions Cl$^-$, I$^-$, Br$^-$, the sulfate anion or anions derived from sulfonic acids such as methansulfonate or p-toluensulfonate.

In the compounds of general formula (I), the aryl group Ar is preferably chosen among:

a) an $Ar_a$ mono- or poly-substituted aryl group, of the most common (±) 2-aryl-propionic acids in current therapeutic use: alminoprofen, benoxaprofen, carprofen, fenbufen, fenoprofen, flurbiprofen, ibuprofen, indoprofen, ketoprofen, loxoprofen, R-naproxen, pirprofen and its dehydro and dihydro derivatives, pranoprofen, surprofen, tiaprofenic acid, zaltoprofen;

b) an aryl-hydroxymethyl-aryl group of formula (IIIa) both as diastereoisomer mixture, or as single diastereoisomers,

wherein, when $Ar_2$ is phenyl $Ar_1$ is selected from the group consisting of phenyl and thien-2-yl while when $Ar_1$ is phenyl, $Ar_2$ is selected from the group consisting of phenyl, 4-thienyl, pyridyl.

c) an aryl of formula (IIIb):

wherein:

$Ar_b$ is a phenyl mono- or poly-substituted by hydroxy, mercapto, $C_1$–$C_3$-alcoxy, $C_1$–$C_3$-alkylthio, chlorine, fluorine, trifluoromethyl, nitro, amino, optionally substituted $C_1$–$C_7$-acylamino;

Φ is hydrogen; a linear or branched $C_1$–$C_5$ alkyl, $C_2$–$C_5$-alkenyl or $C_2$–$C_5$-alkynyl residue optionally substituted by $C_1$–$C_3$-alkoxycarbonyl, substituted or non-substituted phenyl, 2-, 3- or 4-pyridyl, quinolin-2-yl; a $C_3$–$C_6$-cycloalkyl; 2-furyl; 3-tetrahydrofuryl; 2-thiophenyl; 2-tetrahydrothiophenyl or a $C_1$–$C_8$-(alkanoyl, cycloalkanoyl, arylalkanoyl)-$C_1$–$C_5$-alkylamino group e.g. acetyl-N-methyl-amino, pivaloyl-N-ethyl-amino;

d) a 2-(phenylamino)-phenyl of formula (IIIc):

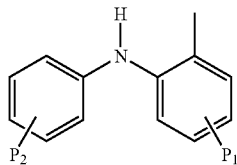

(IIIc)

wherein the substituents $P_1$ and $P_2$ indicate that the two phenyl groups bear, each independently, mono- or poly-substitutions with $C_1$–$C_4$-alkyl, $C_1$–$C_3$-alcoxy groups, chlorine, fluorine and/or trifluoromethyl.

Preferred compounds according to the invention are those wherein:

R is hydrogen;

X is:
a linear $C_1$–$C_6$ alkylene, preferably $C_2$–$C_4$, optionally substituted at $C_1$ by a —$CO_2R_4$ group as defined above;
a linear $C_1$–$C_6$ alkylene optionally substituted at $C_1$ by a —$CONHR_5$ group wherein $R_5$ is OH;
2-butynylene, cis-2-butenylene, trans-2-butenylene;
3-oxa-pentylene, 3-thio-pentylene, 3-oxa-hexylene, 3-thio-hexylene;
$(CH_2)_m$—CO—NH—$(CH_2)_n$— wherein m and n are each independently an integer from 2 to 3;
(CHR')—CONH—$(CH_2)_n$ wherein n is an integer from 2 to 3 and R' is a methyl, having absolute configuration R or S;
a phenyl or phenylmethylene group of formula:

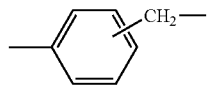

or X, together with the N atom, form an azocycloaliphatic ring, preferably 1-methyl-piperidin-4-yl or 1,5-tropan-3-yl;

Preferred compounds are, in addition, those wherein the $NR_1R_2R_3$ group represents a trimethylammonium, triethylammonium, N-methyl-N,N-diethylammonium, N-methyl-N,N-diisopropylammonium, N-cyclohexylmethyl-N,N-dimethylammonium, N-cyclopentylamino-N,N-dimethylammonium, N-methyl-1-piperidinium, N-ethyl-1-piperidinium, N-methyl-4-morpholinium, N-methyl-4thiomorpholinium, N-benzyl-N,N-dimethylammonium, N-allyl-1-piperidinium, 4-oxy-N-methyl-piperidinium group.

Examples of particularly preferred aryl groups comprise: 4-isobutylphenyl, 4-cyclohexylmethylphenyl, 4-(2-methyl) allyl-phenyl, 3-phenoxyphenyl, 3-benzoyl-phenyl, 3-acetyl-phenyl, the single (R) (S) diastereoisomers and the diastereoisomeric (R,S) mixture of 3-$C_6H_5$—CH(OH)-phenyl, 3-$CH_3$—CH(OH)-phenyl, 5-$C_6H_5$—CH(OH)-thienyl, 4-thienyl-CH(OH)-phenyl, 3-(pyrid-3-yl)-CH(OH)-phenyl, 5-benzoyl-thien-2-yl, 4-thienoyl-phenyl, 3-nicotinoyl-phenyl, 2-fluoro-4-phenyl, 6-metoxy-2-naphthyl, 5-benzoyl-2-acetoxy-phenyl, 5-benzoyl-2-hydroxy-phenyl, 4-cyclopentyl-phenyl, 4-(2-oxo-cyclopentyl)-phenyl, 4-(2-oxo-cyclohexyl)-phenyl.

Particularly preferred aryl groups of formula (IIIb) are phenyl groups 3-substituted by: isoprop-1-en-1-yl, isopropyl, pent-2-en-3-yl; pent-3-yl; 1-phenylethylen-1-yl; α-methylbenzyl.

Particularly preferred aryls of formula (IIIc) are: 2-(2,6-dichloro-phenyl-amino)-phenyl; 2-(2,6-dichloro-phenyl-amino)-5-chloro-phenyl; 2-(2,6-dichloro-3-methyl-phenyl-amino)-phenyl; 2-(3-trifluoromethyl-phenyl-amino)-phenyl. Examples of $P_2$ substituted phenyl groups comprise phenyl groups substituted by one to three halogen atoms, $C_1$–$C_4$ alkyl groups, methoxy, trifluoromethyl, nitro, cyano, haloalkoxy.

Particularly preferred compounds of the invention are:
(R)-{3-[2-(4-isobutylphenyl)-propionylamino]propyl}-trimethylammonium iodide;
(R)-{3-[2-(3-benzoylphenyl)-propionylamino]propyl}-trimethylammonium iodide;
(R)-{3-[2-(4-isobutylphenyl)-propionylamino]propyl}-N-ethyl-N,N-dimethylammonium iodide;
(R)-{3-[2-(4-isobutylphenyl)-propionylamino]propyl}-N-cyclohexylmethyl-N,N-dimethylammonium iodide;
(R)-{3-[2-(4-cyclopentylmethylphenyl)-propionylamino] propyl}-trimethylammonium iodide;
(R)-{3-[2-(3-benzoylphenyl)-propionylamino]propyl}-N-isopropyl-N,N-dimethylammonium iodide;
(R)-{3-[2-(4-isobutylphenyl)-propionylamino]butyl-trimethylammonium iodide;
(R)-{3-[2-(4-isobutylphenyl)-propionylamino]propyl}-1-methyl-piperidinium iodide;
(R)-{3-[2-(3-benzoylphenyl)-propionylamino]propyl}-1-methyl piperidinium iodide;
(R)-{3-[2-(4-isobutylphenyl)-propionylamino]propyl}-4-methyl-morpholinium iodide;
(R)-{3-[2-(3-isopropylphenyl)-propionylamino]propyl}-4-methyl-thiomorpholinium methanesulfonate;
(R)-{3-[2-(4-isobutylphenyl)-propionylamino]ethyl-trimethylammonium bromide;
(R)-2-[(4-isobutylphenyl)-propionylamino]-1,1-dimethyl) piperidinium p-toluenesulfonate;
(R),(S')-2-(4-isobutylphenyl)-N-[(1-carboxy-2"-N,N,N-trimethylammonium)ethyl]propionamide methanesulfonate;
R(−)-2-[(4-isobutylphenyl)-N-(trimethylammoniumethyl) methylamide]propionamide iodide;
(R)(3-{2-[2(2,6-dichlorophenylamino)-phenyl]-propionylamino}-propyl)-trimethylammonium methanesulfonate;
(2R), (4"S) 1-{4-carboxy-4-[2-(4-isobutyl-phenyl)-propionylamino]butyl}-1-methyl-piperidinium iodide;
R(−)-{3-[2-(4'-isobutylphenyl)-propionylamino]-propyl}-(N-benzyl)-N,N-dimethylammonium iodide;
2R-{3-[2-(4'-isobutylphenyl)-propionylamino]-propyl}-(1"methyl-4"carboxyamide) piperidinium iodide;
(2R)-{3-[2-(4'-isobutylphenyl)-propionylamino]-propyl}-(1"-methyl-4"carbonyl) piperidinium iodide;
R(−)-{3,-[-(4'-isobutylphenyl)-propionylamino]-propyl}-triethylammonium iodide;
R(−)-{3-[2-(4'-isobutylphenyl)-propionylamino]-propyl}-1-allylpiperidinium bromide;
R(−)-2-[(4'-isobutyl)phenyl]-N-[4"-N,N,N-trimethylaminophenyl]propionamide iodide;
R(−)-2-[(4'-isobutyl)phenyl]-N-[4"-N,N,N-trimethylaminomethylphenyl]propionamide iodide.

Known methods for the alkylation of tertiary amine groups (Menschutkin reaction) are used for the preparation of formula (I) compounds; compounds of formula (IV), wherein Ar, R, $R_1$, $R_2$ and X are as above defined, are reacted with compounds of formula $R_3Z$ where $R_3$ is defined as above and Z is a conventional leaving group such as chloride, bromide, iodide, methanesulfonate, p-toluensulfonate or sulfate.

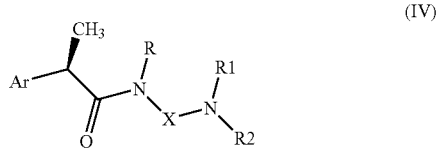

(IV)

The alkylation reactions are normally conducted at room temperature, using conventional protic or aprotic preferably anhydrous solvents or their mixtures, optionally in the presence of a strong non-nucleophilic base. Alternatively, some of compounds of formula (I) can be obtained starting from compounds of formula (IV) by reaction with Michael-type unsaturated substrates catalyzed by mineral acids such as HCl or $HNO_3$.

The preparation of compounds of formula (IV) is described in International Patent Application PCT/EP02/01974. Some of the compounds of formula (IV) are new with respect to specific compounds described in the above patent application, and were prepared with the methods described further below in the Preparations section.

It is understood that is the synthesis of compounds formula (I) starting from the amides of formula (IV) wherein substituents $R_1$ and $R_2$ can be —H independently is included in the process. If desired, the primary and secondary amines can be reacted in the conditions of exhaustive alkylation with compounds of formula $R_3Z$ to yield the compounds of the invention of formula (I) wherein at least two of the residues defined as $R_1$, $R_2$ and $R_3$ are the same. The reaction is carried out under the same conditions as described for the conversion of the amides of formula (IV) into the compounds of the invention of formula (I).

Alternatively, the primary or secondary amides of formula (IV) can be converted into formula (I) compounds in two consecutive steps. In the first step of mono- or dialkylation, the reaction is carried out at room temperature or by heating in the presence of one or two equivalents of $R_2Z$ alkylating agent, depending on the degree of substitution of the starting amine group. The reactions are carried out in conventional protic or aprotic preferably anhydrous solvents or their mixtures, optionally in the presence of a strong non-nucleophilic base.

The compounds of the invention of formula (I) were evaluated in vitro for their ability to inhibit chemotaxis of polymorphonucleate leukocytes (hereinafter referred to as PMNs) and monocytes induced by the fractions of the complement C5a and C5a-desArg. For this purpose, to isolate the PMNs from heparinized human blood, taken from healthy adult volunteers, mononucleates were removed by means of sedimentation on dextran (according to the procedure disclosed by W. J. Ming et al., J. Immunol., 138, 1469, 1987) and red blood cells by a hypotonic solution. The cell vitality was calculated by exclusion with Trypan blue, whilst the ratio of the circulating polymorphonucleates was estimated on the cytocentrifugate after staining with Diff Quick.

Human recombinant fractions C5a and C5a-desArg (Sigma) were used as stimulating agents in the chemotaxis experiments, giving practically identical results.

The lyophilized C5a was dissolved in a volume of HBSS containing 0.2% bovin serum albumin BSA so thus to obtain a stock solution having a concentration of $10^{-5}$ M to be diluted in HBSS to a concentration of $10^{-9}$ M, for the chemotaxis assays.

In the chemotaxis experiments, the PMNs were incubated with the compounds of the invention of formula (I) for 15' at 37° C. in an atmosphere containing 5% $CO_2$.

The chemotactic activity of the C5a was evaluated on human circulating polymorphonucleates (PMNs) resuspended in HBSS at a concentration of $1.5 \times 10^6$ PMNs per mL.

During the chemotaxis assay (according to W. Falket et al., J. Immunol. Methods, 33, 239, 1980) PVP-free filters with a porosity of 5 μm and microchambers suitable for replication were used.

The compounds of the invention in formula (I) were evaluated at a concentration ranging between $10^{-6}$ and $10^{-10}$ M; for this purpose they were added, at the same concentration, both to the lower pores and the upper pores of the microchamber. The wells in the lower part contain the solution of C5a or the simple carrier, those in the upper part contain the suspension of PMNs.

Inhibition of C5a-induced chemotactic activity by the individual compounds of the invention of formula (I) was evaluated by incubating the microchamber for the chemotaxis for 60 min at 37° C. in an atmosphere containing 5% CO2.

Evaluation of the ability of the compounds of the invention of formula (I) to inhibit C5a-induced chemotaxis of human monocytes was carried out according to the method disclosed by Van Damme J. et al. (Eur. J. Immunol., 19, 2367, 1989). Inhibition of C5a-induced chemotactic activity by the individual compounds of the invention of formula (I) towards human monocytes was evaluated at a concentration ranging between $10^{-6}$ and $10^{-10}$ M by incubating the microchamber for the chemotaxis for 120 min. at 37° C. in an atmosphere containing 5% CO2.

By way of example, the inhibition data of the chemotaxis of PMN (C=$10^{-6}$ M) of some representative compounds of the invention are reported in the following table:

| COMPOUND | % INHIBITION (C = $10^{-6}$ M) |
|---|---|
| (R)-(3-{2-[2-(2,6-dielorophenylamino)-phenyl]-propionylamino}-propyl)-trimethylammonium iodide | 62 ± 3 |
| R(-)-{3-[2-(4'-isobutylphenyl)-propionylamino]-propyl}-trimethylammonium iodide | 53 ± 6 |
| R(-)-2-(4'-isobutylphenyl)-propionylamino]-1,1-dimethylpiperidinium iodide | 18 ± 9 |
| R(-)-{3-[2-(4'-isobutylphenyl)-propionylamino]-propyl}-1-methyl-piperidinium iodide | 24 ± 4 |
| R(-)-{3-[2-(4'-isobutylphenyl)-propionylamino]-propyl}-N-cyclohexylmethyl-N,N-dimethyl-ammonium methanesulfonate | 57 ± 4 |
| R(-)-{3-[2-(4'-isobutylphenyl)-propionylamino]-propyl}-(N-benzyil)-N,N-dimethylammonium iodide | 22 ± 4 |

The compounds of formula (I), evaluated ex vivo in the blood in toto according to the procedure disclosed by Patrignani et al., in J. Pharmacol. Exper. Ther., 271, 1705, 1994, were found to be totally ineffective as inhibitors of cyclooxygenase (COX) enzymes.

In almost all cases, the compounds of formula (I) do not interfere with the production of $PGE_2$ induced in murine macrophages by lipopolysaccharides stimulation (LPS, 1 μg/mL) at a concentration ranging between $10^{-5}$ and $10^{-7}$ M. Inhibition of the production of $PGE_2$ which may be recorded, is mostly at the limit of statistical significance, and more often is below 15–20% of the basal value.

It is therefore a further object of the present invention the use of the compounds of the invention as medicaments.

In view of the experimental evidence discussed above and of the role performed by the complement cascade, and namely its fraction C5a, in the processes that involve the activation and the infiltration of neutrophils, the compounds of the invention are particularly useful in the treatment of diseases such as psoriasis (R. J. Nicholoff et al., Am. J. Pathol., 138, 129, 1991), pemphigo and pemphigoid, rheumatoid arthritis (M. Selz et al., J. Clin. Invest., 87, 463, 1981), intestinal chronic inflammatory pathologies such as ulcerative colitis (Y. R. Mahida et al., Clin. Sci., 82, 273, 1992), acute respiratory distress syndrome and idiopathic fibrosis (E. J. Miller, previously cited, and P. C. Carré et al., J. Clin. Invest., 88, 1882, 1991), cystic fibrosis, chronic obstructive pulmonary disease, glomerulonephritis (T. Wada et al., J. Exp. Med., 180, 1135, 1994) and in the prevention and the treatment of injury caused by ischemia and reperfusion.

The compounds of formula (IV) for their use as medicaments are described in International Patent Application PCT/EP02/01974. The new amides of formula (IV) described below in the Preparations section have biological activity comparable to that of amides described in the above patent application and can be used for the treatment of the same pathologies.

To this purpose, the compounds of the invention of formula (I) conveniently are formulated in pharmaceutical compositions using conventional techniques and excipients such as those described in "*Remington's Pharmaceutical Sciences Handbook*" MACK Publishing, New York, 18th ed., 1990.

The compounds of the invention can be administered by intravenous injection, as a bolus, in dermatological preparations (creams, lotions, sprays and ointments), by inhalation as well as orally in the form of capsules, tablets, syrup, controlled-release formulations and the like.

The average daily dose depends on several factors such as the severity of the disease, the condition, age, sex and weight of the patient. The dose will vary generally from 1 to 1500 mg of compounds of formula (I) per day, optionally divided in multiple administrations. Higher doses can be administered for long periods of time, thanks to the low toxicity of compounds of the invention.

The following examples and preparations serve to illustrate the invention.

By convention, apices (e.g. R', S', S" etc.) show the absolute configurations present in substituent $R_1$ in the compounds of the invention of formula (I). Abbreviations: THF: tetrahydrofuran; DMF: dimethylformamide; EtAc: ethyl acetate, HOBZ: hydroxybenzotriazol, DCC:dicyclohexylcarbodiimide.

Materials and Methods

The amines used as reagents in the synthesis of compounds of formula (IV) are known products, generally commercially available or they can be prepared according to methods described in the literature.

The synthesis of 2-aryl-propionic acids of formula $\phi\text{-Ar}_3\text{—C}(CH_3)H\text{—}CO_2H$ and of their R-enantiomers is reported in International patent application PCT/EP01/01285.

The optical resolution was carried out by means of salification with R(+)-N-methylbenzylamine according to the method described by Akguen et al., Arzneim. Forsch., 46:9 891–894, 1996.

PREPARATIONS

Preparation of Omega-aminoalkylamides of R-2-arylpropionic acid as Intermediates The preparation of compounds of formula (IV) is disclosed in International Patent application PCT/EP02/01974. Some compounds of formula (IV) are new and described for the first time in the present patent application.

Examples of the preparation of the new amides of formula (IV) are reported below.

Preparation 1

R(−)-2-[(3-benzoyl)phenyl]-N-[3"-(N',N'-dimethylamino)propyl]propionamide

Hydroxybenzotriazol (0.604 g, 3.93 mmol) and N,N-dicyclohexylcarbodiimide (0.81 g, 3.93 mmol) are added to a solution of R(−)-ketoprofen (1 g, 3.93 mmol) in anhydrous dichloromethane (25 mL). The mixture is stirred at r.t. for 30 min; N,N-dimethyl-1,3-propandiamine (0.49 mL, 3.93 mmol) is added to the suspension formed. The resulting suspension is stirred at r.t. overnight. Dicyclohexylurea (DCU) is then filtered off under vacuum and the filtrate is evaporated at reduced pressure; the crude oily residue is taken up in acetonitrile (20 mL) and the mixture left overnight at T=4° C. After the filtration of a further aliquot of DCU, the filtrate is again evaporated at reduced pressure and the residue is purified by means of flash chromatography on silica gel (eluent $CHCl_3/CH_3OH$ 8:2); R(−)-2-[(3'-benzoyl)phenyl]-N-[3"-(N',N'-dimethylamino)propyl]-propionamide (0.997 g, 2.94 mmol) is obtained as a transparent oil.

Yield 75%

$[\alpha]_D = -20$ (c=0.9; $CH_3OH$)

$^1$H-NMR ($CDCl_3$) δ 7.90–7.40 (m, 9H); 7.25 (s, 1H, CONH); 3.65 (m, 1H); 3.36 (m, 2H); 2.38 (m, 2H); 2.20 (s, 6H); 1.62 (m, 5H).

In a similar way the following compounds were also prepared:

R(−)-2-[(3'-benzoyl)phenyl]-N-(3"-N'"-piperidinopropyl)-propionamide

Yield 80%

$[\alpha]_D = -47.5$ (c=0.3; $CH_3OH$)

$^1$H-NMR ($CDCl_3$) δ 7.85–7.42 (m, 9H+CONH); 3.80 (m, 1H); 3.57–3.28 (m, 4H); 2.85 (m, 2H); 2.10 (m, 2H); 1.65 (m, 11H).

R(−)-2-[(4'-isobutyl)phenyl]-N-[3"-N'-(4",4"-piperidinediol)-propyl]-propionamide $[\alpha]_D = -19.5$ (c=1; $CH_3OH$)

$^1$H-NMR (DMSO-d6) δ 8.05 (t, 1H, J=6 Hz, CONH); 7.25 (d, 2H, J=8 Hz); 7.08 (d, 2H, J=8 Hz); 3.55 (m, 1H); 3.40 (m, 2H); 3.35–3.25 (m, 6H); 2.38 (d, 2H, J=7Hz); 2.05 (m, 4H); 1.85 (m, 1H); 1.50 (m, 2H); 1.35 (d, 3H, J=7 Hz); 0.87 (d, 6H, J=7 Hz).

R(−)-2-[(4'-isobutyl)phenyl]-N-[3''-N'-(4''-carboxyamidopiperidin)-propyl]propionamide

[α]$_D$=−28.5 (c=1; CH$_3$OH)

$^1$H-NMR (DMSO-d6) δ 8.45 (d, 2H, J=8 Hz), CONH2); 8.10 (t, 1H, J=6 Hz, CONH); 7.35 (d, 2H, J=8 Hz); 7.20 (d, 2H, J=8 Hz); 3.65 (m, 1H); 3.42 (m, 2H); 3.15–2.90 (m, 6H); 2.35 (d, 2H, J=7 Hz); 2.15 (m, 1H); 1.80 (m, 1H); 1.55 (m, 6H); 1.35 (d, 3H, J=7 Hz); 0.85 (d, 6H, J=7 Hz).

R(−)-2-[(4'-isobutyl)phenyl]-N-[4''-N,N-dimethylaminomethylphenyl]-propionamide

[α]$_D$=−35 (c=1; CH$_3$OH)

$^1$H-NMR (CDCl$_3$): δ 7.82 (dd, 1H, J$_1$=8.4 Hz, J$_2$=2 Hz); 7.55 (d, 1H, J=2 Hz); 7.20 (m, 2H); 7.10 (m, 2H); 6.85 (d, 2H, J=8.4 Hz); 6.15 (bs, 1H, CONH); 3.70 (s, 2H); 3.50 (m, 1H); 3.20 (s, 6H); 2.45 (d, 2H, J=7 Hz); 1.88 (m, 1H); 1.50 (d, 3H, J=7 Hz); 0.85 (d, 6H, J=7 Hz).

EXAMPLES

Quaternary Salts of Omega-aminoalkylamides of R-2-Aryl-Propionic Acids

Example 1

R(−)-{3-[2-(4'-isobutylphenyl)-propionylamino]-propyl}-1-methyl-piperidinium iodide R(−)-2-[(4'-isobutyl)phenyl]-N-[3''-N'-(N'-methyl)piperidinopropyl]-propionamide (0.095 g; 0.287 mmol) is dissolved in anhydrous tetrahydrofuran (6 mL) under inert atmosphere. Methyl iodide (0.1 mL, 1.61 mmol) is added to the solution; the solution is stirred at r.t. for 18 hours until the starting reagent is no longer detectable. The solvent is then evaporated at reduced pressure and the residue is taken up in isopropyl ether. A white precipitate forms which is stirred for 6 hours. The precipitate is filtered and dried under vacuum at T=40° C. to yield the R(−)-2-[(4'-isobutyl)phenyl]-N-[3''-N'-(N'-methyl)-piperidinopropyl]propionamide iodide (0.114 g; 0.24 mmol) as a clear yellow waxy solid.

Yield 84%

[α]$_D$=−12 (c=0.7; CH$_3$OH)

$^1$H-NMR (DMSO-d$_6$) δ 8.05 (t, 1H, J=6 Hz, CONH); 7.25 (d, 2H, J=8 Hz); 7.08 (d, 2H, J=8 Hz); 3.55 (m, 1H); 3.25–3.02 (m, 8H); 2.90 (s, 3H); 2.38 (d, 2H, J=7 Hz); 1.85–1.55 (m, 7H); 1.50 (m, 2H); 1.35 (d, 3H, J=7 Hz); 0.88 (d, 6H, J=7 Hz).

The following compounds were prepared by using the method reported above:

R(−)-{3-[2-(4'-isobutylphenyl)-propionylamino]-propyl}-trimetilammonium iodide m.p. 105–110° C.

[α]$_D$=−17 (c=1.0; CH$_3$OH)

$^1$H-NMR (CDCl$_3$) δ 7.42 (d, 2H, J=8 Hz); 7.20 (t, 1H, J=6 Hz, CONH); 7.07 (d, 2H, J=8 Hz); 3.83 (m, 1H); 3.77 (m, 2H); 3.55–3.20 (m, 2H); 3.18 (s, 9H); 2.40 (d, 2H, J=7 Hz); 2.05 (m, 2H); 1.83 (m, 1H); 1.45 (d, 3H, J=7 Hz); 0.9 (d, 6H, J=7 Hz).

R(−)-{3-[2-(4'-isobutylphenyl)-propionylamino]-butyl}-trimethylammonium iodide m.p. 100–103° C.

[α]$_D$=−25 (c=1.0; CH$_3$OH)

$^1$H-NMR (CDCl$_3$) δ 7.25 (d, 2H, J=8 Hz); 7.09 (d, 2H, J=8 Hz); 6.18 (s, 1H, CONH); 3.61 (m, 1H); 3.28 (m, 2H); 3.12 (m, 2H); 3.08 (s, 9H); 2.44 (d, 2H, J=7 Hz); 1.81 (m, 1H); 1.75 (m, 4H); 1.50 (d, 3H, J=7 Hz); 0.88 (d, 6H, J=7 Hz).

R(−)-2-[(4'-isobutylphenyl)-propionylamino]-1,1-dimethylpiperidinium iodide m.p. 80–85° C.

[α]$_D$=−7 (c=1.2; CH$_3$OH)

$^1$H-NMR (DMSO-d$_6$) δ 7.91 (d, 1H, J=7 Hz, CONH); 7.22 (d, 2H, J=8 Hz); 7.08 (d, 2H, J=8 Hz); 3.80 (m, 1H); 3.53 (m, 1H); 3.35–3.30 (m, 4H); 3.08 (s, 3H); 3.00 (s, 3H); 2.40 (d, 2H, J=7 Hz); 1.95–1.65 (m, 5H); 1.3 (d, 3H, J=7 Hz); 0.87 (d, 6H, J=7 Hz).

R(−)-{3-[2-(4'-isobutylphenyl)-propionylamino]-propyl}-4-methylmorpholinium iodide m.p. 84–87° C.

[α]$_D$=−17 (c=0.5; CH$_3$OH)

1H-NMR (CDCl$_3$) δ 7.45 (d, 2H, J=8 Hz); 7.02 (m, 3H, CONH+2Har.); 4.25 (m, 2H); 3.92 (m, 1H); 3.88 (m, 1H); 3.80 (m, 1H); 3.53 (m, 1H); 3.35 (m, 2H); 3.15 (m, 1H); 3.00 (s, 3H); 2.92–2.70 (m, 4H); 2.40 (d, 2H, J=7 Hz); 2.15 (m, 2H); 1.88 (m, 1H); 1.45 (d, 3H, J=7 Hz); 0.92 (d, 6H, J=7 Hz).

R(−)-2-[(4'-isobutylphenyl)-N-(trimethylammoniumethyl)-methylamide]-propionamide iodide m.p. 70–72° C.

[α]$_D$=−18 (c=1.0; CH3OH)

1H-NMR (DMSO-d$_6$) δ 7.22 (d, 2H, J=8 Hz); 7.11 (d, 2H, J=8 Hz); 6.25 (bs, 2H, CONH); 3.57 (m, 1H); 3.30 (m, 2H); 3.10 (s, 9H); 2.45 (d, 2H, J=7 Hz); 2.40 (m, 2H); 1.88 (m, 1H); 1.75 (m, 2H); 1.52 (d, 3H, J=7 Hz); 0.92 (d, 6H, J=7 Hz).

R(−)-{3-[2-(3'-benzoylphenyl)-propionylamino]-propyl}-trimethylammonium iodide m.p. 62–65° C.

[α]$_D$=−16.3 (c=1.0; CH$_3$OH)

$^1$H-NMR (DMSO-d6) δ 8.20 (t, 1H, J=7 Hz, CONH); 7.81–7.47 (m, 9H); 3.75 (m, 1H); 3.27–3.05 (m, 4H); 3.00 (s, 9H); 1.85 (m, 2H); 1.37 (d, 3H, J=7 Hz).

R(−)-{3-[2-(3-benzoylphenyl)propionylamino]-propyl)]-1-methylpiperidinium iodide m.p. 69–73° C.

[α]$_D$=−10 (c=0.6; CH$_3$OH)

$^1$H-NMR (DMSO-d$_6$) δ 8.18 (t, 1H, J=7 Hz, CONH); 7.80–7.47 (m, 9H); 3.70 (m, 1H); 3.28–3.05 (m, 8H); 2.92 (s, 3H); 1.87–1.53 (m, 6H); 1.42 (m, 2H); 1.38 (d, 3H, J=7 Hz).

(R)-{3-{2-[2-(2,6-dichlorophenylamino)-phenyl]-propionylamino}-propyl)-trimethylammonium iodide

[α]$_D$=−15 (c=1.0; CH$_3$OH)

$^1$H-NMR (DMSO-d$_6$) δ 8.48 (m, 1H, CONH); 8.27 (s, 1H, NH); 7.52 (d, 2H, J=8 Hz); 7.18 (q, 2H, J1=8 Hz, J2=16 Hz); 7.05 (t, 1H, J=7 Hz); 6.88 (t, 1H, J=7 Hz); 6.30 (d, 1H, J=8 Hz); 3.75 (m, 1H); 3.30 (m, 11H); 3.21 (m, 2H); 1.88 (m, 2H); 1.64 (d, 3H, J=7 Hz).

(2R),(4''S) 1-{4-carboxy-4-[2-(4-isobutyl-phenyl)-propionylamino]-butyl}-1-methyl-piperidinium iodide

[α]$_D$=−9.5 (c=1.0; CH$_3$OH)

$^1$H-NMR (DMSO-d$_6$): δ 8.66 (bs, 1H, CONH); 7.22 (d, 2H, J=8 Hz); 7.5 (d, 2H, J=8 Hz); 4.00 (m, 1H); 3.80 (m, 1H); 2.95 (m, 6H); 2.90 (s, 3H); 2.45 (d, 2H, J=7 Hz); 1.82 (m, 1H); 1.70–1.33 (m, 10H); 1.31 (d, 3H, J=7 Hz); 0.89 (d, 6H, J=7 Hz).

(2R)-{3-[2-(4'-isobutylphenyl)-propionylamino]-propyl}-(1"-methyl-4"carbonyl)-piperidinium iodide

[α]$_D$=−39 (c=1; CH$_3$OH)
$^1$H-NMR (DMSO-d6) δ 8.15 (t, 1H, J=6 Hz, CONH); 7.28 (d, 2H, J=8 Hz); 7.12 (d, 2H, J=8 Hz); 3.80 (m, 1H); 3.70 (m, 2H); 3.35–3.25 (m, 6H); 3.18 (s, 3H); 2.35 (d, 2H, J=7 Hz); 2.12 (m, 4H); 1.85 (m, 1H); 1.50 (m, 2H); 1.37 (d, 3H, J=7 Hz); 0.87 (d, 6H, J=7 Hz).

2R-{3-[2-(4'-isobutylphenyl)-propionylamino]-propyl}-(1"-methyl-4"-carboxyamide)-piperidinium iodide

[α]$_D$=−25 (c=1; CH$_3$OH)
$^1$H-NMR (DMSO-d6) δ 8.74 (d, 2H, J=8 Hz, CONH2); 8.18 (t, 1H, J=6 Hz, CONH) 7.30 (d, 2H, J=8 Hz); 7.22 (d, 2H, J=8 Hz); 3.75 (m, 1H); 3.45 (m, 2H); 3.35 (s, 3H); 3.20–3.00 (m, 6H); 2.38 (d, 2H, J=7 Hz); 2.15 (m, 1H); 1.90 (m, 1H); 1.75 (m, 6H); 1.35 (d, 3H, J=7 Hz); 0.85 (d, 6H, J=7 Hz).

R(−)-2-[(4'-isobutyl)-phenyl]-N-[4"-N,N,N-trimethylaminomethylphenyl]-propionamide iodide

[α]$_D$=−23 (c=1; CH$_3$OH)
$^1$H-NMR (DMSO-d$_6$): δ 7.80 (dd, 1H, J$_1$=8.4 Hz, J$_2$=2 Hz); 7.55 (d, 1H, J=2 Hz); 7.24 (m, 2H); 7.10 (m, 2H); 7.00 (d, 2H, J=8.4 Hz); 6.20 (bs, 1H, CONH); 3.70 (s, 2H); 3.50 (m, 1H); 3.20 (s, 9H); 2.45 (d, 2H, J=7 Hz); 1.88 (m, 1H); 1.50 (d, 3H, J=7 Hz); 0.85 (d, 6H, J=7 Hz).

Example 2

The following compound was prepared according to the method described in Example 1, but using ethyliodide as the reagent:

R(−)-{3-[2-(4'-isobutylphenyl)-propionylamino]-propyl}triethylammonium iodide m.p. 100–102° C.
[α]$_D$=−19.5 (c=1.0; CH$_3$OH)
$^1$H-NMR (CDCl$_3$) δ 7.43 (d, 2H, J=8 Hz); 7.22 (t, 1H, J=6 Hz, CONH); 7.10 (d, 2H, J=8 Hz); 3.83 (m, 1H); 3.77 (m, 2H); 3.55–3.35 (m, 2H); 3.15 (q, 6H, J=7 Hz); 2.95 (t, 9H, J=7 Hz); 2.42 (d, 2H, J=7 Hz); 2.05 (m, 2H); 1.85 (m, 1H); 1.45 (d, 3H, J=7 Hz); 0.9 (d, 6H, J=7 Hz).

Example 3

The following compound was prepared according to the method described in Example 1, but using benzyliodide as the reagent:

R(−)-{3-[2-(4'-isobutylphenyl)-propionylamino]-propyl}-(N-benzyl)-N,N-dimethylammonium iodide m.p. 97–100° C.
[α]$_D$=−12 (c=1.0; CH$_3$OH)
$^1$H-NMR (CDCl$_3$) δ 7.42 (d, 2H, J=8 Hz); 7.30–7.25 (m, 5H); 7.20 (t, 1H, J=6 Hz, CONH); 7.07 (d, 2H, J=8 Hz); 3.85 (m, 1H); 3.72 (m, 2H); 3.68 (s, 2H); 3.55–3.32 (m, 2H); 3.20 (s, 6H); 2.40 (d, 2H, J=7 Hz); 2.05 (m, 2H); 1.83 (m, 1H); 1.45 (d, 3H, J=7 Hz); 0.9 (d, 6H, J=7 Hz).

Example 4

The following compound was prepared according to the method described in Example 1, but using cyclohexylmethyl metanesulfonate as the reagent:

R(−)-{3-[2-(4'-isobutylphenyl)-propionylamino]-propyl}-N-cyclohexylmethyl-N,N-dimethyl-ammonium metaneosulfonate

[α]$_D$=−23 (c=1.0; CH$_3$OH)
$^1$H-NMR (DMSO-d$_6$) δ 7.44 (d, 2H, J=8 Hz); 7.20 (t, 1H, J=6 Hz, CONH); 7.08 (d, 2H, J=8 Hz); 3.83 (m, 1H); 3.77 (m, 2H); 3.55–3.20 (m, 4H); 3.18 (s, 6H); 3.00 (s, 3H); 2.40 (d, 2H, J=7 Hz); 2.05 (m, 2H); 1.83 (m, 1H); 1.75 (m, 5H); 1.48 (m, 1H); 1.45 (d, 3H, J=7 Hz); 1.22 (m, 3H); 0.95 (m, 2H); 0.9 (d, 6H, J=7 Hz).

Example 5

The following compound was prepared according to the method described in Example 1, but using allyl bromide in lieu of methyl iodide R(−)-{3-[2-(4'-isobutylphenyl)-propionylamino]-propyl}-1-allylpiperidinium bromide

[α]$_D$=−14.5 (c=0.5; CH$_3$OH)
$^1$H-NMR (DMSO-d6) δ 8.05 (t, 1H, J=6 Hz, CONH); 7.25 (d, 2H, J=8 Hz); 7.08 (d, 2H, J=8 Hz); 6.05 (m, 1H); 5.35 (d, 1H, J=2 Hz); 5.15 (d, 1H, J=2 Hz); 3.80 (d, 2H, J=7 Hz); 3.55 (m, 1H); 3.25–3.02 (m, 8H); 2.38 (d, 2H, J=7 Hz); 1.85–1.55 (m, 7H); 1.50 (m, 2H); 1.35 (d, 3H, J=7 Hz); 0.88 (d, 6H, J=7 Hz).

Example 6

The following compound was prepared starting from the (4-aminophenyl)trimethylammonium iodide hydrochloride (commercial reagent):

R(−)-2-[(4'-isobutyl)phenyl]-N-[4"-NNN-trimethylaminophenyl]-propionamide iodide Hydroxybenzotriazol (0.62 g; 4.58 mmol) is added, at T=0° C., to a solution of (R)(−)Ibuprofen (1.01 g; 5 mmol) in DMF (4.5 mL). The solution is stirred at T=0° C. for 30 min; (4-aminophenyl)-trimethylammonium iodide hydrochloride (1.433 g; 4.56 mmol) is then added to the mixture. N,N-dicyclohexylcarbodiimmide (1.02 g; 4.95 mmol) is added gradually in small portions. After stirring at T=0° C. for 2 h., the mixture is left to warm to r.t. Then it is stirred for 24 h. The DCU which is formed is filtered off and DMF is distilled off under reduced pressure. The residue is dissolved in H$_2$O and stirred in diisopropyl ether (30 mL) overnight at room temperature; the precipitate formed is filtered under vacuum and dried in oven at T=40° C. for 6 h, yielding a white solid (1.67 g; 3.58 mmol);

[α]$_D$=−31 (c=1; CH$_3$OH)
$^1$H-NMR (DMSO-d$_6$): δ 7.85 (dd, 1H, J$_1$=8.4 Hz, J$_2$=2 Hz); 7.62 (d, 1H, J=2 Hz); 7.24 (m, 2H); 7.10 (m, 2H); 7.02 (d, 2H, J=8.4 Hz); 6.15 (bs, 1H, CONH); 3.50 (m, 1H); 3.25 (s, 9H); 2.45 (d, 2H, J=7 Hz); 1.85 (m, 1H); 1.52 (d, 3H, J=7 Hz); 0.90 (d, 6H, J=7 Hz).

The invention claimed is:

1. A (R)-2-aryl-propionamide compound of formula (I):

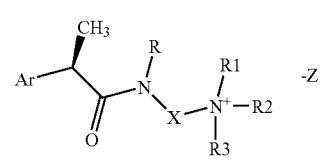

(I)

wherein

Ar represents a substituted or non-substituted aryl group;
R represents hydrogen, C$_1$–C$_4$ alkyl, C$_2$–C$_4$ alkenyl, C$_2$–C$_4$ alkynyl, optionally substituted by a CO$_2$R$_4$ group, wherein R$_4$ represents hydrogen or a linear or branched C$_1$–C$_6$ alkyl group or a linear or branched C$_2$–C$_6$ alkenyl group;

X represents:

linear or branched $C_1$–$C_6$ alkylene, $C_4$–$C_6$ alkenylene, $C_4$–$C_6$ alkynylene, optionally substituted by a $CO_2R_4$ group or by a $CONHR_5$ group wherein $R_5$ represents hydrogen, linear or branched $C_2$–$C_6$ alkyl or an $OR_4$ group, $R_4$ being defined as above;

phenyl or a phenylmethylene group of formula:

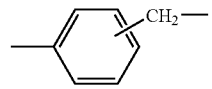

a $(CH_2)_m$—B—$(CH_2)_n$, group, optionally substituted by a $CO_2R_4$ or $CONHR_5$ group, as defined above, wherein B is an oxygen or sulfur atom, m is zero or an integer from 2 to 3 and n is an integer from 2 to 3; or B is a CO, SO or CONH group, m is an integer from 1 to 3 and n is an integer from 2 to 3;

or X together with the nitrogen atom to which it is bound and with the $R_1$ group forms a nitrogen containing 3–7 membered heterocyclic monocyclic or polycyclic ring;

$R_1$, $R_2$ and $R_3$ are independently linear or branched $C_1$–$C_6$ alkyl, optionally substituted by an oxygen or sulfur atom, a $C_3$–$C_7$ cycloalkyl, $C_3$–$C_6$ alkenyl, $C_3$–$C_6$-alkynyl, aryl, aryl-$C_1$–$C_3$-alkyl, hydroxy-$C_2$–$C_3$-alkyl group;

or $R_1$ and $R_2$ together with the N atom to which they are bound, form a nitrogen containing 3–7 membered heterocyclic ring of formula (II) and $R_3$ independently has the meanings as defined above,

(II)

wherein Y represents a single bond, a methylene group, an oxygen atom, a nitrogen atom or a sulfur atom and p represents an integer from 0 to 3;

$Z^-$ represents a pharmaceutically acceptable counter-ion of quaternary ammonium salts, with the proviso that when Ar is biphenyl, $R_2$ and $R_3$ are not ethyl.

2. The compound according to claim 1, wherein Ar is selected from a) an $Ar_a$ mono- or poly-substituted aryl group of (±) 2-aryl-propionic acids selected in the group consisting of alminoprofen, benoxaprofen, carprofen, fenbufen, fenoprofen, flurbiprofen, ibuprofen, indoprofen, ketoprofen, loxoprofen, R-naproxen, pirprofen and its dehydro and dihydro derivatives, pranoprofen, surprofen, tiaprofenic acid, zaltoprofen;

b) an aryl-hydroxymethyl-aryl group of formula (IIIa) both as diastereoisomer mixture, or as single diastereoisomers,

(IIIa)

wherein, when $Ar_2$ is phenyl $Ar_1$ is selected from the group consisting of phenyl and thien-2-yl while when $Ar_1$ is phenyl, $Ar_2$ is selected from the group consisting of phenyl, 4-thienyl, pyridyl.

c) an aryl of formula (IIIb):

(IIIb)

wherein:

$Ar_b$ is a phenyl mono- or poly-substituted by hydroxy, mercapto, $C_1$–$C_3$-alcoxy, $C_1$–$C_3$-alkylthio, chlorine, fluorine, trifluoromethyl, nitro, amino, optionally substituted $C_1$–$C_7$-acylamino;

Φ is hydrogen; a linear or branched $C_1$–$C_5$ alkyl, $C_2$–$C_5$-alkenyl or $C_2$–$C_5$-alkynyl residue optionally substituted by $C_1$–$C_3$-alkoxycarbonyl, substituted or non-substituted phenyl, 2-, 3- or 4-pyridyl, quinolin-2-yl; a $C_3$–$C_6$-cycloalkyl; 2-furyl; 3-tetrahydrofuryl; 2-thiophenyl; 2-tetrahydrothiophenyl or a a $C_1$–$C_8$-(alkanoyl, cycloalkanoyl, arylalkanoyl)-$C_1$–$C_5$-alkylamino group e.g. acetyl-N-methyl-amino, pivaloyl-N-ethyl-amino; and d) a 2-(phenylamino)-phenyl of formula (IIIc):

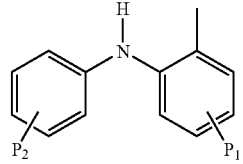

(IIIc)

wherein the substituents $P_1$ and $P_2$ indicate that the two phenyl groups bear, each independently, mono- or poly-substitutions with $C_1$–$C_4$-alkyl, $C_1$–$C_3$-alcoxy groups, chlorine, fluorine and/or trifluoromethyl.

3. The compound according to any one of claims 1 and 2 wherein:

R is hydrogen;

X is:

a linear $C_1$–$C_6$ alkylene, preferably $C_2$–$C_4$, optionally substituted at $C_1$ by a —$CO_2R_4$ group as defined above;

a linear $C_1$–$C_6$ alkylene optionally substituted at $C_1$ by a —$CONHR_5$ group wherein $R_5$ is OH;

2-butynylene, cis-2-butenylene, trans-2-butenylene;

3-oxa-pentylene, 3-thio-pentylene, 3-oxa-hexylene, 3-thio-hexylene;

$(CH_2)_m$—CO—NH—$(CH_2)_n$— wherein m and n are each independently an integer from 2 to 3;

(CHR')—CONH—$(CH_2)_n$ wherein n is an integer from 2 to 3 and R' is a methyl, having absolute configuration R or S;

a phenyl or phenylmethylene group of formula:

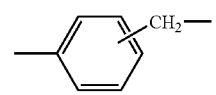

or X, together with the N atom, form an azocycloaliphatic ring.

4. The compound according to claim 3, wherein X is a linear $C_2$–$C_4$ alkylene.

5. The compound according to any one of claims 1 and 2, wherein $NR_1R_2R_3$ group represents a trimethylammonium, triethylammonium, N-methyl-N,N-diethylammonium, N-methyl-N,N-diisopropylammonium, N-cyclohexylmethyl-N,N-dimethylammonium, N-cyclopentylamino-N,N- dimethylammonium, N-methyl-1-piperidinium, N-ethyl-1-piperidinium, N-methyl-4-morpholinium, N-methyl-4 thiomorpholinium, N-benzyl-N,N-dimethylammonium, N-allyl-1-piperidinium, 4-oxy-N-methyl-piperidinium group or X together with the amine N to which it is bound and with the $R_1$ group, forms a nitrogen containing 5–6 membered heterocyclic ring and the substituents $R_2$ and $R_3$ represent independently a methyl or cyclohexyl residue.

6. The compound according to any one of claims 1 and 2, wherein Ar is selected from 4-isobutylphenyl, 4-cyclohexylmethylphenyl, 4-(2-methyl)allyl-phenyl, 3-phenoxyphenyl, 3-benzoyl-phenyl, 3-acetyl-phenyl, the single (R) (S) diastereoisomers and the diastereoisomeric (R,S) mixture of 3-$C_6H_5$—CH(OH)-phenyl, 3-$CH_3$—CH(OH)-phenyl, 5-$C_6H_5$—CH(OH)-thienyl, 4-thienyl-CH(OH)-phenyl, 3-(pyrid-3-yl)-CH(OH)-phenyl, 5-benzoyl-thien-2-yl, 4-thienoyl-phenyl, 3-nicotinoyl-phenyl, 2-fluoro-4-phenyl, 6-metoxy-2-naphtyl, 5-benzoyl-2-acetoxy-phenyl, 5-benzoyl-2-hydroxy-phenyl, 4-cyclopentyl-phenyl, 4-(2-oxo-cyclopentyl)-phenyl, 4-(2-oxo-cyclohexyl)-phenyl.

7. The compound according to claim 1, wherein Ar is a phenyl group 3-substituted by isoprop-1-en-1-yl-isopropyl, pent-2-en-3-yl, pent-3-yl; 1-phenylethylen-1-yl; α-methylbenzyl.

8. The compound according to claim 1, wherein the Ar groups in the formula (IIIc) are 2-(2,6-dichloro-phenylamino)-phenyl; 2-(2,6-dichlorophenyl-amino)-5-chlorophenyl; 2-(2,6-dichloro-3-methyl-phenyl-amino)-phenyl; 2-(3-trifluoromethyl-phenylamino)-phenyl.

9. The compound according to claim 1, wherein $Z^-$ is a halide chosen from $Cl^-$, $I^-$, $Br^-$, a sulfate anion, methanesulfonate or p-toluenesulfonate.

10. The compound according to claim 1, selected from:
(R)-{3-[2-(4-isobutylphenyl)-propionylamino]propyl}-trimethylammonium iodide;
(R)-{3-[2-(3-benzoylphenyl)-propionylamino]propyl}-trimethylammonium iodide;
(R)-{3-[2-(4-isobutylphenyl)-propionylamino]propyl}-N-ethyl-N,N-dimethylammonium iodide;
(R)-{3-[2-(4-isobutylphenyl)-propionylamino]propyl}-N-cyclohexylmethyl-N,N-dimethylammonium iodide;
(R)-{3-[2-(4-cyclopentylmethylphenyl)-propionylamino]propyl}-trimethylammonium iodide;
(R)-{3-[2-(3-benzoylphenyl)-propionylamino]propyl}-N-isopropyl-N,N-dimethylammonium iodide;
(R)-{3-[2-(4-isobutylphenyl)-propionylamino]butyl-trimethylammonium iodide;
(R)-{3-[2-(4-isobutylphenyl)-propionylamino]propyl}-1-methyl-piperidinium iodide;
(R)-{3-[2-(3-benzoylphenyl)-propionylamino]propyl}-1-methyl piperidinium iodide;
(R)-{3-[2-(4-isobutylphenyl)-propionylamino]propyl}-4-methyl-morpholinium iodide;
(R)-{3-[2-(3-isopropylphenyl)-propionylamino]propyl}-4-methyl-thiomorpholinium methanesulfonate;
(R)-{3-[2-(4-isobutylphenyl)-propionylamino]ethyl-trimethylammonium bromide;
(R)-2-[(4-isobutylphenyl)-propionylamino]-1,1-dimethyl)piperidinium p-toluenesulfonate;
(R),(S')-2-(4-isobutylphenyl)-N-[(1-carboxy-2"-N,N,N-trimethylammonium)ethyl]propionamide methanesulfonate;
R(−)-2-[(4-isobutylphenyl)-N-(trimethylammoniumethyl) methylamide]propionamide iodide;
(R)(3-{2-[2(2,6-dichlorophenylamino)-phenyl]-propionylamino}-propyl)-trimethylammonium methanesulfonate;
(2R),(4"S)1-{4-carboxy-4-[2-(4-isobutyl-phenyl)-propionylamino]butyl}-1-methyl-piperidinium iodide;
R(−)-{3-[2-(4'-isobutylphenyl)-propionylamino]-propyl}-(N-benzyl)-N,N-dimethylammonium iodide;
2R-{3-[2-(4'-isobutylphenyl)-propionylamino]-propyl}-(1"methyl-4"carboxyamide) piperidinium iodide;
(2R)-{3-[2-(4'-isobutylphenyl)-propionylamino]-propyl}-(1"-methyl-4" carbonyl) piperidinium iodide;
R(−)-{3,-[-(4'-isobutylphenyl)-propionylamino]-propyl}-triethylammonium iodide;
R(−)-{3-[2-(4'-isobutylphenyl)-propionylamino]-propyl}-1-allylpiperidinium bromide;
R(−)-2-[(4'-isobutyl)phenyl]-N-[4"-N,N,N-trimethylaminophenyl]propionamide iodide; and
R(−)-2-[(4'-isobutyl)phenyl]-N-[4"-N,N,N-trimethylaminomethylphenyl]propionamide iodide.

11. A medicament comprising the compound according to claim 1.

12. A method for inhibiting chemotaxis of neutrophils and monocytes induced by C5a in a subject in need thereof, comprising the step of administering the compound according to claim 1 to said subject, wherein said compound inhibits chemotaxis of neutrophils and monocytes induced by C5a.

13. A method for treating psoriasis, pemphigus and pemphigoid, rheumatoid arthritis, intestinal chronic inflammatory pathologies including ulcerative colitis, acute respiratory distress syndrome, idiopathic fibrosis, cystic fibrosis, chronic obstructive pulmonary disease and/or glomerulonephritis in a subject in need thereof, comprising the step of administering the compound according to claim 1 to said subject.

14. A method for preventing or treating an injury caused by ischemia and reperfusion in a subject in need thereof, comprising the step of administering the compound according to claim 1 to said subject.

15. Pharmaceutical compositions containing a compound according to claim 1 in admixture with a suitable carrier thereof.

16. A process for the preparation of a (R)-2-aryl-propionamide compound of formula (I):

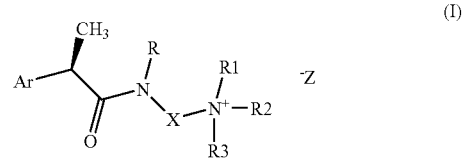

wherein Ar, X, $R_1$, $R_2$, $R_3$ have the meaning as defined in claim 1, comprising reacting amides of formula (IV)

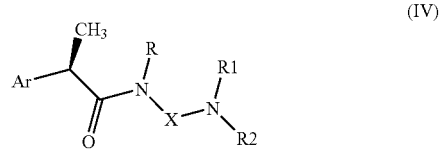

with compounds of formula $R_3Z$, wherein Z is a conventional leaving group.

17. The process according to claim 16, wherein the conventional leaving group is selected from the group consisting of chloride, bromide, iodide, methanesulfonate, p-toluensulfonate, and sulfate.